United States Patent
Buckner

(10) Patent No.: US 10,046,262 B2
(45) Date of Patent: Aug. 14, 2018

(54) METHOD AND SYSTEM TO EXCAVATE AND REMOVE UNDERGROUND NOXIOUS VAPORS

(71) Applicant: VAC-TRON EQUIPMENT, LLC, Aurora, CO (US)

(72) Inventor: Don M Buckner, Okahumpka, FL (US)

(73) Assignee: VAC-TRON EQUIPMENT, LLC, Okahumpka, FL (US)

(*) Notice: Subject to any disclaimer, the term of this patent is extended or adjusted under 35 U.S.C. 154(b) by 92 days.

(21) Appl. No.: 14/643,179

(22) Filed: Mar. 10, 2015

(65) Prior Publication Data

US 2015/0266068 A1 Sep. 24, 2015

Related U.S. Application Data

(60) Provisional application No. 61/955,385, filed on Mar. 19, 2014.

(51) Int. Cl.
| | |
|---|---|
| *B01D 46/00* | (2006.01) |
| *G01N 33/22* | (2006.01) |
| *B09B 1/00* | (2006.01) |
| *B09C 1/00* | (2006.01) |

(52) U.S. Cl.
CPC ..... *B01D 46/0091* (2013.01); *B01D 46/0019* (2013.01); *B09B 1/006* (2013.01); *B09C 1/005* (2013.01); *G01N 33/227* (2013.01); *B09C 2101/00* (2013.01)

(58) Field of Classification Search
CPC ............ B01D 46/0091; B01D 46/0019; B09B 1/006; B09C 1/005; B09C 2101/00; G01N 33/227

USPC ....................................................... 405/128.2
See application file for complete search history.

(56) References Cited

U.S. PATENT DOCUMENTS

| | | | |
|---|---|---|---|
| 4,183,407 A | 1/1980 | Knopik | |
| RE33,102 E | 10/1989 | Visser et al. | |
| 5,076,360 A | 12/1991 | Morrow | |
| 5,111,883 A | 5/1992 | Savery | |
| 5,118,629 A | 6/1992 | Quiros et al. | |
| 5,221,159 A * | 6/1993 | Billings | ............... B09C 1/00 |
| | | | 166/246 |
| 5,332,333 A | 7/1994 | Bentley | |
| 5,361,855 A | 11/1994 | Schuermann et al. | |
| 5,439,594 A | 8/1995 | Regan et al. | |
| 5,591,244 A | 1/1997 | Vross et al. | |

(Continued)

*Primary Examiner* — Amber R Anderson
*Assistant Examiner* — Patrick F Lambe
(74) *Attorney, Agent, or Firm* — Matthew G. McKinney, Esq.; Allen, Dyer et al.

(57) ABSTRACT

A system to excavate and remove underground noxious vapors includes a suction wand in fluid communication with a debris tank. A collar is fitted around the suction wand and is configured to seal noxious vapors within a hole around the suction wand. A primary valve is used to control whether the suction wand is being used to excavate material to send to the debris tank, or whether the suction wand is being used to remove noxious vapors from the hole to send to a filtration unit. A monitor is configured to detect explosive concentrates in the noxious vapors to determine whether the explosive concentrates exceed an acceptable level. In addition, the system is configured to dilute and filter the noxious vapors before discharging to the atmosphere.

17 Claims, 3 Drawing Sheets

(56) References Cited

U.S. PATENT DOCUMENTS

| | | | | |
|---|---|---|---|---|
| 5,709,505 A | * | 1/1998 | Williams | B09C 1/005 |
| | | | | 166/268 |
| 8,858,124 B2 | | 10/2014 | Lamonte | |
| 2007/0104540 A1 | * | 5/2007 | Howard | B09B 1/004 |
| | | | | 405/128.25 |
| 2010/0239373 A1 | * | 9/2010 | Gillecriosd | B01D 53/002 |
| | | | | 405/128.5 |
| 2014/0020268 A1 | * | 1/2014 | Buckner | E02F 3/8891 |
| | | | | 37/304 |

* cited by examiner

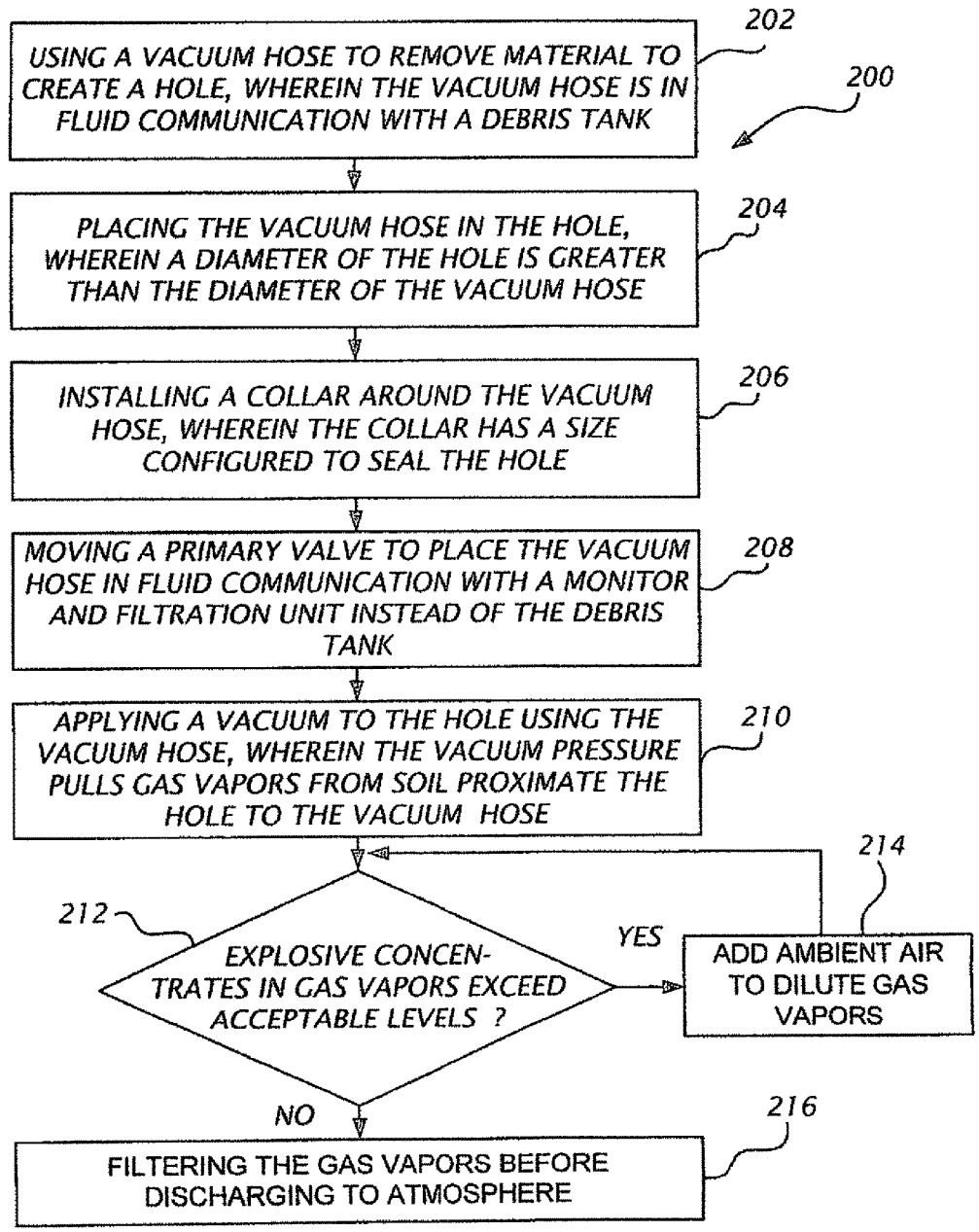

METHOD AND SYSTEM TO EXCAVATE AND REMOVE UNDERGROUND NOXIOUS VAPORS

I. CROSS REFERENCE TO RELATED APPLICATION

This application claims the benefit of U.S. Provisional Patent Application Ser. No. 61/955,385, filed on Mar. 19, 2014, the contents of which are herein incorporated by reference in their entirety.

II. FIELD

The present invention relates in general to a method and system to excavate and remove underground noxious vapors.

III. DESCRIPTION OF RELATED ART

Industrial vacuum equipment has dozens of wet and dry uses such as locating underground utilities (potholing), hydro excavation, air excavation and vacuum excavation. In addition, the equipment can be used for directional drilling slurry removal, industrial clean-up, waste clean-up, lateral and storm drain clean-out, oil spill clean-up and other natural disaster clean-up applications. The vacuum systems may be mounted to a truck or trailer and are typically powered by gas or diesel engines. Often times noxious vapors or other particulates are released into the ambient air during excavating of contaminated groundwater and soils. In addition, considering the vast number of current and former industrial, commercial, and waste processing facilities in the United States capable of causing volatile organic or inorganic groundwater or soil contamination, contaminant exposure via vapor intrusion is a significant risk to the public.

Accordingly, what is needed is a method and system to excavate and remove underground noxious vapors. However, in view of the prior art at the time the present invention was made, it was not obvious to those of ordinary skill in the pertinent art how the identified needs could be fulfilled.

IV. SUMMARY

A method and system to excavate and remove underground noxious vapors is disclosed. In a particular embodiment, the system includes a suction wand to first excavate material. A collar is fitted around the suction wand, where the collar is sized and shaped to prevent noxious vapors from being released from the hole around the suction wand. A monitor is configured to detect explosive concentrates in the noxious vapors to determine whether the explosive concentrates exceed an acceptable level. In addition, an air valve is configured to add ambient air to the noxious vapors in order to reduce the explosive concentrates. The system also includes a filtration unit in fluid communication with the suction wand, where the filtration unit is used to treat the noxious vapors separately from the excavated material. A primary valve is configured to direct a flow of excavated materials from the suction wand to a debris tank when the primary valve is in an excavation position and will direct a flow of the noxious vapors from the suction wand to the filtration unit when the primary valve is turned to a filtration position. The system also includes a recirculation conduit in fluid communication with the air valve and configured to cycle the noxious vapors from the monitor to the air valve and back to the monitor until the explosive concentrates are below the acceptable level.

In another particular illustrative embodiment, the method includes placing a vacuum hose in a hole and using a collar around the vacuum hose to seal the hole around the vacuum hose. A vacuum pressure is applied to the hole using the vacuum hose, where the vacuum pressure pulls noxious vapors from soil proximate the hole into the vacuum hose. The method also includes adding ambient air to dilute the noxious vapors if explosive concentrates in the noxious vapors exceed a predetermined acceptable level. In addition, the method includes filtering the noxious vapors to remove volatile organic compounds or volatile inorganic compounds before discharging in the atmosphere.

Other aspects, advantages, and features of the present disclosure will become apparent after review of the entire application, including the following sections: Brief Description of the Drawings, Detailed Description, and the Claims.

V. BRIEF DESCRIPTION OF THE DRAWINGS

FIG. 4 is a flow diagram of a method to excavate and remove underground noxious vapors.

VI. DETAILED DESCRIPTION

The word "exemplary" is used herein to mean "serving as an example, instance, or illustration." Any embodiment or design described herein as "exemplary" is not necessarily to be construed as preferred or advantageous over other embodiments or designs.

Figure 1:
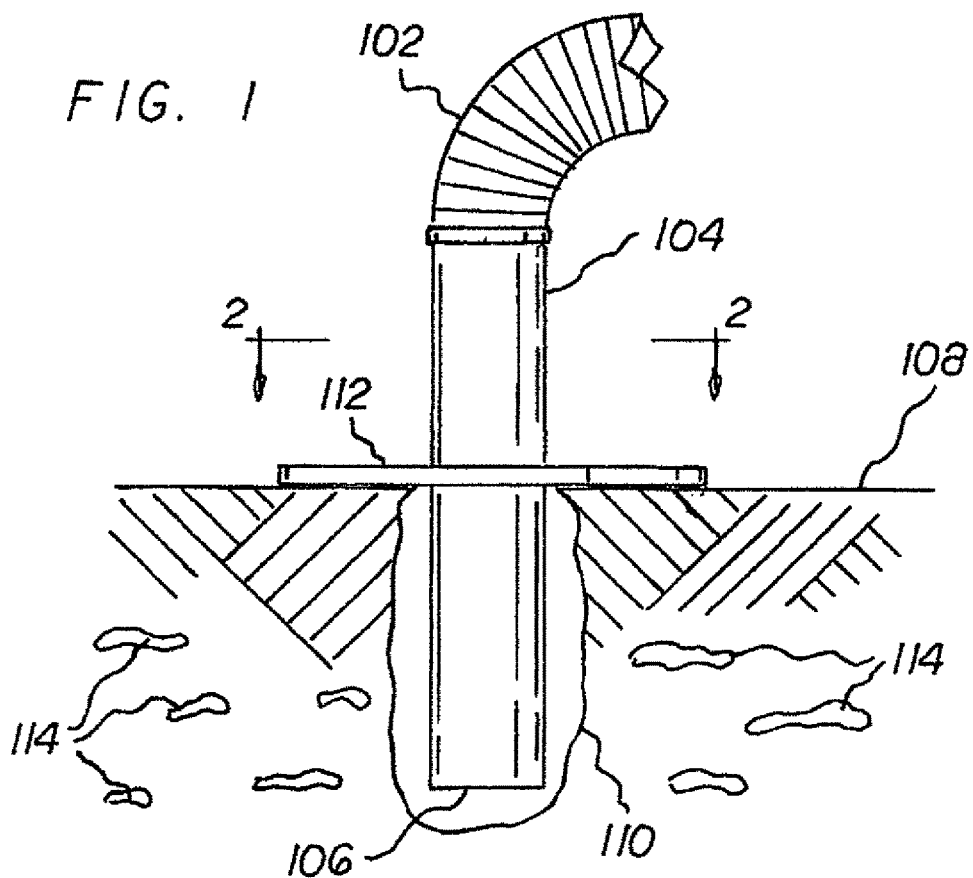
FIG. 1 is an elevation view of a suction wand and collar of a particular illustrative embodiment of a system to excavate and remove underground noxious vapors.
Figure 2:
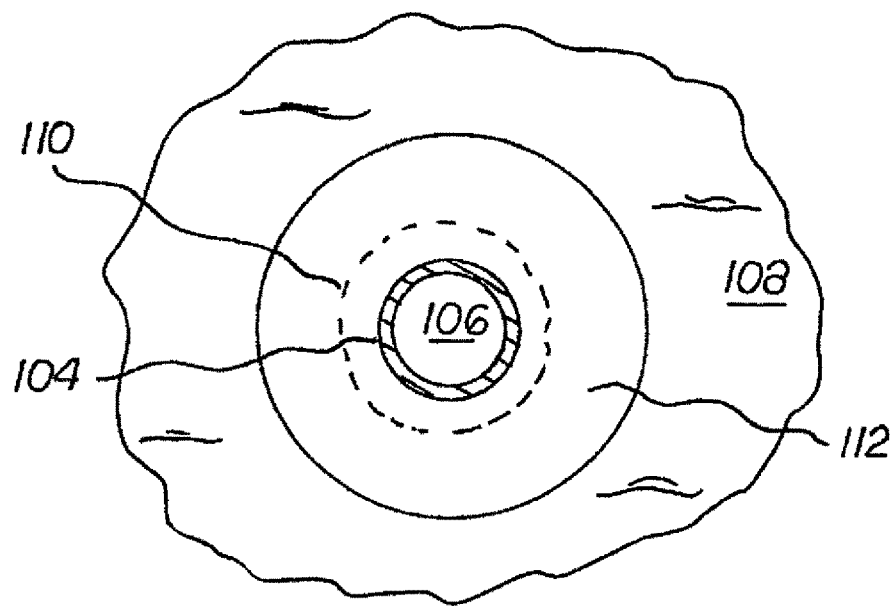
FIG. 2 is a top view of the suction wand and collar shown in FIG. 1 taken in the direction of line 2-2.

Referring to FIGS. 1 and 2, a particular illustrative embodiment of a system to excavate and remove underground noxious vapors is disclosed. The system includes a vacuum hose 102 that is secured to a suction wand 104. The vacuum hose 102 is in fluid communication with a pump that provides suction to the vacuum hose 102 to remove soil, water, and other materials that are being excavated from a site to form a hole 110 in the ground 108. The excavated materials are subsequently collected in a debris tank. During and/or after the excavated materials are removed, often times noxious vapors 114 that are in the ground 108 are released into the atmosphere through the hole 110. This can be hazardous if the vapors 114 are explosive or otherwise volatile in nature.

In order to prevent the noxious vapors 114 from being released, a collar 112 is fitted around the suction wand 104. The width of the collar 112 is the same width or greater than the width of the hole 110 at the ground surface in order to seal the hole 110 around the suction wand 104. Once the collar 112 is in place, the open end 106 of the suction wand 104 is used to capture and remove noxious vapors 114 that may be released in the hole 110. The noxious vapors 114 in the soil 108 around the hole move towards the hole 110 as the suction is applied. A filtration unit 130 is in fluid communication with the vacuum hose 102, where the filtration unit 130 is used to treat the noxious vapors 114 before releasing into the atmosphere.

Figure 3:
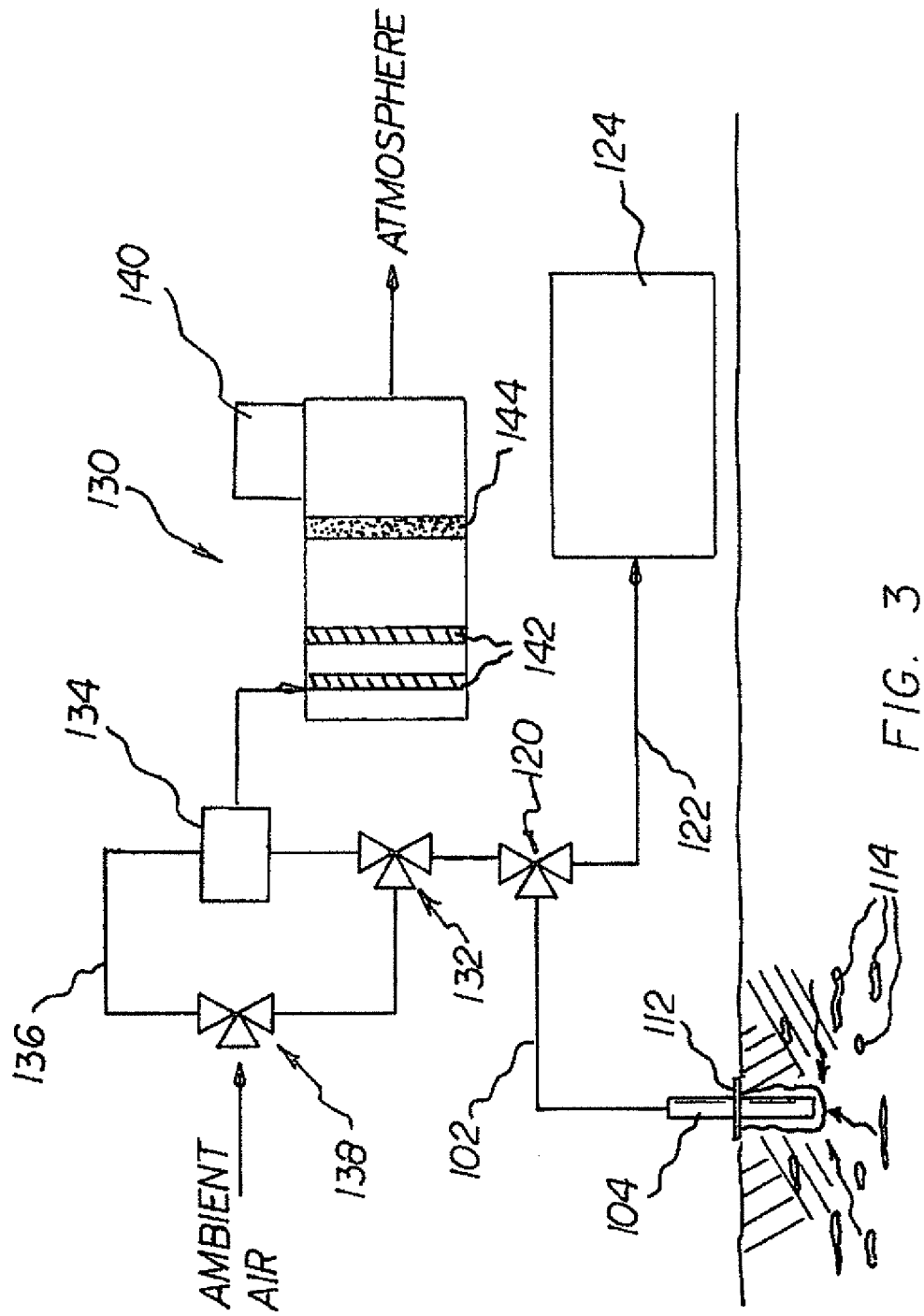
FIG. 3 is a schematic of the system to excavate and remove underground noxious vapors.

Referring now to FIG. 3, a primary valve 120 controls the flow of excavated materials to the debris tank 124 via conduit 122 and the noxious vapors 114 to the filtration unit 130. In operation the suction wand 104 is used to excavate materials to form the hole 110. The excavated materials are directed from the suction wand 104, through the vacuum hose 102 to the primary valve 120 in an excavation position, and into the debris tank 124 via conduit 122. Once the materials are excavated, the primary valve 120 is moved to a filtration position so that the flow from the suction wand 104 is now through the vacuum hose 102, to the primary valve 120 in the filtration position, and to the filtration unit 130. When the primary valve 120 is positioned in the filtration position, the flow through the vacuum hose 102 is substantially gaseous and not solids or liquids.

A monitor 134 is used to detect explosive concentrates in the vapors 114 to determine whether the explosive concentrates exceed acceptable levels. If the explosive concentrates exceed acceptable levels, then ambient air is added by opening air valve 138 to dilute the noxious vapors 114. A recirculation conduit 136 is used to cycle the vapors 114 from the monitor 134 to the air valve 138 to a secondary valve 132 and back to the monitor 134. The noxious vapors 114 continue to cycle and ambient air is continued to be added until the explosive concentrates are within acceptable levels.

Once the monitor 134 determines that the noxious vapors 114 are within acceptable levels, the noxious vapors 114 are directed through a first filter 142 to remove larger particles, oil, grease and solvent residues. The noxious vapors 114 then pass through a second filter 144 to remove odors and any remaining volatile compounds before discharging the filtered vapors into the atmosphere. Additional or alternative filters may be used such as a HEPA filter, or the use of paper or bag filters. A blower 140 may be used to control the flow through the filtration unit 130. The blower 140 may draw the noxious vapors through the filters 142, 144 and discharge the filtered air into the atmosphere. The blower 140 may be driven by an engine or electric motor, for example. The filtered air is discharged into the atmosphere free of the most harmful particulates, odors and other volatile contaminants. The blower 140 creates a negative pressure within the filtration unit 130 in order to draw the noxious vapors 114 through the filters 142, 144.

A flow diagram of a particular embodiment of a method to excavate and remove underground noxious vapors is described in FIG. 4 and generally designated 200. At 202, a vacuum hose is used to remove material to create a hole, where the vacuum hose is in communication with a debris tank. Moving to 204, the vacuum hose is placed in the hole, where a diameter of the hole is greater than the diameter of the vacuum hose. A collar is used, at 206, around the vacuum hose, where the collar has a size configured to seal the hole. At 208, a primary valve is moved to place the vacuum hose in fluid communication with a monitor and filtration unit instead of the debris tank. A vacuum is applied, at 210, to the hole using the vacuum hose, where the vacuum pressure pulls noxious vapors from the soils proximate the hole to the vacuum hose. If explosive concentrates in the noxious vapors exceed acceptable levels, at 212, the ambient air is added to dilute the noxious vapors, at 214. The noxious vapors are then filtered, at 216, before discharging the filtered air to the atmosphere.

The previous description of the disclosed embodiments is provided to enable any person skilled in the art to make or use the disclosed embodiments. Various modifications to these embodiments will be readily apparent to those skilled in the art, and the principles defined herein may be applied to other embodiments without departing from the scope of the disclosure. Thus, the present disclosure is not intended to be limited to the embodiments shown herein but is to be accorded the widest scope possible consistent with the principles and novel features.

What is claimed is:

1. A system to excavate and remove underground noxious vapors, the system comprising:
    a primary valve having an inlet, a first outlet, and a second outlet, the primary valve configured to switch between an operation to excavate soil to an operation to remove the underground noxious vapors;
    a vacuum hose having a first end and a second end, the first end coupled to the inlet of the primary valve;
    a suction wand coupled to a second end of the vacuum hose;
    a debris tank coupled to the first outlet of the primary valve and configured to receive the soil that is excavated from a site to form a hole in a ground surface with the suction wand;
    a collar fitted around the suction wand, wherein the collar is sized and shaped to prevent noxious vapors from being released from around the suction wand when the suction wand is positioned in the hole;
    a secondary valve having an inlet, a first outlet, and a second outlet, wherein the inlet of the secondary valve is coupled to the second outlet of the primary valve;
    a filtration unit;
    a monitor coupled to the filtration unit and the first outlet of the secondary valve and configured to detect explosive concentrates in the noxious vapors to determine whether the explosive concentrates exceed an acceptable level before discharging to the filtration unit;
    an air valve having an inlet to ambient air outside the hole and separate from the suction wand, the air valve coupled to the second outlet of the secondary valve and configured to add the ambient air from outside the hole to the noxious vapors in order to dilute the explosive concentrates upstream of the filtration unit; and
    a conduit coupled to the air valve and monitor;
    wherein the air valve is configured to add the ambient air from outside the hole to the conduit before discharging the noxious vapors to the filtration unit when the secondary valve diverts the noxious vapors to the air valve via the second outlet of the secondary valve.

2. The system of claim 1, wherein the filtration unit is used to treat the noxious vapors.

3. The system of claim 1, wherein the primary valve is configured to direct a flow of the excavated soil from the suction wand to the debris tank when the primary valve is in an excavation position and to direct a flow of the noxious vapors from the suction wand to the filtration unit when the primary valve is in a filtration position.

4. The system of claim 1, the filtration unit further comprising a first filter.

5. The system of claim 4, the filtration unit further comprising a blower to draw the noxious vapors through the first filter and into an atmosphere.

6. The system of claim 5, wherein the first filter is configured to remove volatile organic compounds or volatile inorganic compounds from the noxious vapors.

7. The system of claim 6, wherein the debris tank and filtration unit are mounted to a trailer.

8. The system of claim 7, wherein the first filter is a mesh filter for removing oil, grease, and solvent residues from the noxious vapors.

9. The system of claim 8, the filtration unit further comprising a second filter, wherein the second filter is a carbon filter.

10. The system of claim 9, further comprising directing a flow of the excavated soil from the vacuum hose to the debris tank when a primary valve is in an excavation position and directing a flow of the noxious vapors from the vacuum hose to the filtration unit when the primary valve is turned to a filtration position.

11. A method to excavate and remove underground noxious vapors, the method comprising:
   excavating soil from a site to form a hole in a ground surface with a vacuum hose in communication with a debris tank;
   placing the vacuum hose in the hole having a void between the vacuum hose and the hole, wherein a diameter of the hole is greater than the diameter of the vacuum hose;
   using a collar around the vacuum hose to seal the hole around the vacuum hose;
   applying a vacuum to the hole using the vacuum hose, wherein a vacuum pressure pulls noxious vapors from soil proximate the hole to the vacuum hose;
   adding ambient air from outside the hole and separate from the vacuum hose to dilute the noxious vapors upstream of a filtering unit if explosive concentrates in the noxious vapors exceed a predetermined acceptable level;
   continuing to add the ambient air from outside the hole to the noxious vapors until the explosive concentrates no longer exceed the predetermined acceptable level; and
   filtering the noxious vapors before discharging in the atmosphere.

12. The method of claim 11, further comprising moving a primary valve to place the vacuum hose in fluid communication with a monitor and the filtration unit instead of the debris tank.

13. The method of claim 12, further comprising monitoring the noxious vapors to determine whether the explosive concentrates in the noxious vapors exceed the predetermined acceptable level.

14. The method of claim 13, further comprising removing volatile organic compounds or volatile inorganic compounds from the noxious vapors.

15. The method of claim 14, wherein the filtration unit comprises a first filter for removing oil, grease, and solvent residues from the noxious vapors.

16. The method of claim 15, wherein a second filter of the filtration unit is a carbon filter.

17. A system to excavate and remove underground noxious vapors, the system comprising:
   a suction wand in fluid communication with a pump;
   a collar fitted around the suction wand;
   an air valve having an inlet to ambient air separate from the suction wand and configured to add the ambient air to the noxious vapors in order to dilute the noxious vapors;
   a filtration unit downstream of the air valve to treat the noxious vapors;
   a monitor coupled upstream of the filtration unit;
   a conduit in fluid communication with the air valve and configured to add the ambient air to the noxious vapors before discharging the noxious vapors to the filtration unit;
   a debris tank configured to receive soil that is excavated from a site to form a hole in a ground surface with the suction wand; and
   a primary valve configured to direct a flow of the excavated soil from the suction wand to the debris tank when the primary valve is in an excavation position and to direct a flow of the noxious vapors from the suction wand to the filtration unit when the primary valve is in a filtration position.

* * * * *